US005736573A

United States Patent [19]
Galat

[11] Patent Number: 5,736,573
[45] Date of Patent: Apr. 7, 1998

[54] LIPID AND WATER SOLUBLE DERIVATIVES OF DRUGS

[76] Inventor: Alexander Galat, 126 Buckingham Rd., Yonkers, N.Y. 10701

[21] Appl. No.: 688,515

[22] Filed: Jul. 31, 1996

[51] Int. Cl.$^6$ ..................................... A01N 37/00
[52] U.S. Cl. ..................... 514/560; 514/282; 514/558; 546/45; 562/450
[58] Field of Search .................. 514/282, 558, 514/653, 560; 546/45; 562/509, 510, 450; 564/355, 366

[56] References Cited

U.S. PATENT DOCUMENTS

| | | | |
|---|---|---|---|
| 3,769,319 | 10/1973 | Boltz et al. | 560/30 |
| 4,141,897 | 2/1979 | Olofson et al. | 546/45 |
| 4,828,837 | 5/1989 | Uster et al. | 424/450 |
| 4,917,896 | 4/1990 | Peck et al. | 424/449 |
| 5,204,339 | 4/1993 | Minaskanian et al. | 514/182 |
| 5,413,794 | 5/1995 | Suzuki et al. | 424/449 |

OTHER PUBLICATIONS

Gummer, C.L. in Percutaneous Absorption: Mechanisms–Methodology–Drug Delivery, Marcel Dekker Inc., edited by Bronaugh, R.L. et al, pp. 561–570, Jan. 1987.

Morrison, R.T., et al, Organic Chemistry, 4th edition, Allyn & Bacon Inc., 1983, pp. 891 and 926.

*Primary Examiner*—C. Warren Ivy
*Assistant Examiner*—Garth M. Dahlen
*Attorney, Agent, or Firm*—Bryan, Levitin & Bab,LLP

[57] ABSTRACT

Amine compound derivatives enhancing the transdermal delivery (skin penetration) of pharmacologically active substances (drugs). In order to pass through the skin more effectively, the present invention provides derivatives that are soluble or miscible, or compatible with both lipids and water. These derivatives are formed by combining a drug of the amine class (to which most drugs belong) with a lipid-soluble long-chain acid such as oleic, linoleic, stearic, myristic, or palmitic acid.

8 Claims, No Drawings

LIPID AND WATER SOLUBLE DERIVATIVES OF DRUGS

FIELD AND BACKGROUND OF THE INVENTION

The present invention relates to new derivatives of drugs of the amine class having special solubility characteristics suitable for transdermal delivery. The chemical composition of these new derivatives is so designed that the molecular structure responsible for a drug's pharmacological activity remains unchanged; only the solubility characteristics are altered.

In the history of drug development, major efforts were concentrated on the preparation of water-soluble forms. This was because most drugs are administered orally, and solubility in water is necessary to facilitate absorption from the gastro-intestinal tract.

Since most drugs chemically belong to the amine group, such soluble forms were easily prepared by synthesizing the acid-addition salts, such as hydrochlorides, sulfates, phosphates, maleates, malates, cirates, tartrates, peruvates, acetates, succinates, gluconates, etc. These salts are not only water-soluble, but they are also crystalline, which facilitates their synthesis, isolation, purification and the preparation of solid dosage forms, usually as tablets.

However, while the solubility of drugs in water alone is sufficient in most cases to insure effectiveness of the oral administration, a different kind of solubility characteristics is required if it is desired to use an alternative route such as the skin as the portal for drug entry.

The transdermal application of drugs offers many important advantages over the oral route. Orally ingested drugs are subject to partial decomposition and deactivation in the gastro-intestinal tract caused by the action of hydrochloric acid, alkalinity, hydrolysis, enzymes, and other substances present there. Transdermally applied drugs are not affected this way. Further, the transdermal route is beneficial since the transdermal route avoids one pass through the liver where other undesirable biochemical transformations and deactivation take place.

Patients with behavioral and addiction problems such as obesity, alcoholism, and drug addiction, often resist treatment with orally-administered drugs. A special advantage of treatment of these conditions via transdermal delivery is to insure far greater patient compliance.

Despite these important advantages, only a very few of the hundreds of drugs available in medicine today are applied transdermally. The reason for this is that most drugs penetrate the skin very poorly or not at all. To pass through the skin, a substance must penetrate two major barriers that protect the animal body against invasion by foreign substances such as bacteria, viruses and toxic products including, of course, medicines and drugs. One barrier of the skin is a lipid layer, and the other is a hydrophilic layer. Therefore, for a drug to penetrate the skin it must be soluble in both lipids and water. Most of the acid-addition salts of drugs used in medicine today are soluble in water only. They are essentially insoluble in lipids, and therefore cannot penetrate the skin to reach the blood and exert their pharmacological effect. This explains why the transdermal route of drugs, despite its important advantages, is not widely used in medicine.

SUMMARY OF THE INVENTION

It is an object of the present invention to provide derivatives of drugs, which are soluble in both lipids and aqueous media, thus greatly enhancing their skin penetration. The terms "lipid" and "oil", as well as "solubility", miscibility", and "compatibility", are used interchangeably herein.

Accordingly, compositions exhibiting such altered solubility characteristics and improved skin penetration can be achieved by combining a drug of the amine type in its free-base form with-long-chain oil-soluble acids such as oleic, linoleic, stearic, myristic, or palmitic acid.

When amine derivatives of the invention are used to deliver medications transdermally, several benefits are realized. First, the action of the drug is not affected by substances present in the gastrointestinal tract or by action of the liver on the drug. Secondly, the total dosage of the active component of the drug can be reduced, since a greater concentration of the drug is delivered more effectively using the amine derivative of the invention.

For example, when the appetite suppressant phenylpropanolamine is prepared in the amine derivative form according to this invention, a standard 75 mg daily dosage may be reduced to about 10 mg when this amine drug is delivered transdermally. This reduces undesirable side effects considerably.

Yet a further benefit of transdermal application of drug derivatives of the present invention is the ease of application for people who are negligent and would otherwise skip or miss taking a dose of the drug. By transdermally applying the drug, the patient does not have to remember to take one or more pills every day, and can instead rely on the release of the drug into his or her system over an extended period of time, such as 10–20 days.

Since most drugs chemically belong to the amine group, the present invention can be applied to many areas of pharmacology such as appetite-suppressants (anorexics), hypertension remedies, alcohol antagonists, analgesics, anesthetics, antiarrhythmic, anti-inflammatories, dermatitis remedies, nausea medications and others.

The various features of novelty which characterize the invention are pointed out with particularity in the claims annexed to and forming a part of this disclosure. For a better understanding of the invention, its operating advantages and specific objects attained by its uses, reference is made to the following preferred embodiments illustrating the present invention.

DESCRIPTION OF THE PREFERRED EMBODIMENTS

The amine class drug derivatives of the invention are formed by combining the free base form of an amine compound with an oil-soluble acid.

The free-base form of the amine may be obtained by the reaction of its acid-addition salt with alkalis, or by other known methods.

The amine in the form of its free base is then combined with an oil-soluble acid to form an amine derivative which exhibits the property of solubility in lipids.

The derivative can then be used with any known transdermal device, such as a transdermal patch, to deliver the drug to a patient needing it.

The following example illustrates the preparation of derivative related to this invention. It describes the preparation and properties as they pertain to the drug phenylpropanolamine.

Phenylpropanolamine used in this example has several pharmacological actions: decongestant, appetite-suppressant anorexic), and bronchodilator.

Similar derivatives suitable for transdermal application can be formed with the alcohol-antagonist 17-(Cyclopropylmethyl)-4,5-epoxy-3,14dihydroxymorphinan-6-one, commercially available as Naltrexone, and Trexan, hypotensive agents, (hypertension remedies), analgesics, anesthetics, antiarrhythmics, anti-inflammatories, dermatitis remedies, and nausea medications, among others.

EXAMPLE

Step One

Preparation of Phenylpropanolamine Base

First, a free-base form of an amine compound, phenylpropanolamine was obtained using the material amounts as specified below.

| Phenylpropanolamine Hydrochloride | 100 g |
|---|---|
| Water | 300 ml |

Phenylpropanolamine hydrochloride was dissolved in the water and to this solution there was added, rapidly with stirring, 20 gm of sodium hydroxide dissolved in 100 ml of water. The mixture was allowed to stand at 10° C. overnight. Crystals of the free base were filtered, washed with water and dried in vacuum over calcium chloride. This process yielded 59 gm of free base phenylpropanolamine.

Step Two

Combination of Phenylpropanolamine and Oleic Acid

Next, the free base was combined with oleic acid, a long chain oil-soluble acid, in the following proportions:

| Phenylpropanolamine | 10 g | |
|---|---|---|
| Oleic acid | 20 g | (Theory: 18.7 g) |

The oleic acid was heated to about 90° C. in a-water-bath and phenyl propanolamine amine base was added in small portions with stirring. A clear, slightly brownish fluid was formed that solidified at room temperature to a waxy mass. The new product exhibited the following solubility characteristics:

Dissolves in water forming a clear solution or gel;

Solubility in propylene glycol: 2 parts (wt) in 1 part (vol); and

Solubility in isopropyl palmitate: ca. 15%

A solution of 2 g of the phenylpropanolamineoleic acid in 1 ml of propylene glycol is miscible with isopropyl palmitate in all proportions. A solution of 2 g in 1 ml of propylene glycol and 1.5 ml of isopropyl palmitate remains clear on addition of 0.25 ml of water.

In contrast to water-solubility, it is difficult to measure lipid-solubility, the solubility of substance in lipid-like media such as isopropyl palmitate indirectly provides a useful indication of its solubility in lipids. Acid-addition salts of drugs in which the acids used are those described above (i.e. hydrochloric, sulfuric, phosphoric, etc) are insoluble in isopropyl palmitate and other lipid-like media, and therefore cannot penetrate the lipid layer of the skin, or at least penetrate it to an extent sufficient for it to be useful in transdermal delivery.

The solubility of the products of this invention in propylene glycol is of importance since this solvent is commonly used in known transdermal delivery to increase skin penetration. As mentioned, the solubility of phenylpropanolamine-oleic acid in propylene glycol is two parts in one part of solvent, a solubility of almost 70%. Such high concentrations are seldom encountered in transdermal delivery. The importance of obtaining high concentrations of the drug in solution derives from the fact that skin penetrability is a direct function of concentration; therefore, the unusually high concentrations exhibited by the products of the present invention strongly propel the transported drug through the skin.

In particular, the value of the transdermal phenylpropanolamine derivative as an appetite-suppressant is noteworthy. Since percutaneous delivery is continuous and steady, constant blood levels can be maintained around the clock. Moreover, a small patch can deliver medication for weeks. Users are more likely to prefer placing a small dime-size patch on the skin once or twice a month, instead of taking 15–30 pills.

Of related interest is fenfluramine, whose pharmacological action attenuates carbohydrate craving in humans, and thus exhibits an anti-obesity effect. Being an amine, fenfluramine readily forms a lipid-/water-soluble derivative analogous to that formed by phenylpropanolamine, as described in the example above.

While a specific embodiment of the invention has been shown and described in detail to illustrate the application of the principles of the invention, it will be understood that the invention may be embodied otherwise without departing from such principles.

What is claimed is:

1. An amine derivative compound for transdermal delivery to humans exhibiting solubility in both oils and water, the compound comprising a free base amine moiety chemically bonded with a natural oil-soluble, long-chain aliphatic acid which is non-toxic to humans, wherein the amine moiety comprises one of phenylpropanolamine, fenfluramine, and 17-(cyclopropylmethyl)-4,5-epoxy-3,14dihydroxymorphinan-6-one.

2. An amine derivative compound according to claim 1, wherein the aliphatic acid is one of oleic acid, linoleic acid, stearic acid, myristic acid, and palmitic acid.

3. A method of preparing an amine derivative compound for transdermal delivery which is soluble in both oils and water, the method comprising:

providing an amine in free base form, wherein the amine comprises one of one of phenylpropanolamine, fenfluramine, and 17-(cyclopropylmethly)-4,5-epoxy-3,14-dihydroxymorphinan-6one;

providing a natural oil-soluble, long-chain aliphatic acid which is non-toxic to humans; and reacting the amine in free base form with the aliphatic acid to form the amine derivative compound.

4. A method according to claim 3, wherein the aliphatic acid comprises one of oleic acid, linoleic acid, stearic acid, myristic acid, and palmitic acid.

5. An amine derivative compound exhibiting solubility in both oils and water, the compound comprising a free base amine moiety chemically bonded with an oil-soluble, long-chain aliphatic acid, wherein the amine moiety comprises one of phenylpropanolamine, fenfluramine, and 17-(cyclopropylmethyl)-4-5-epoxy-3,14dihydroxymorphinan-6-one.

6. An amine derivative compound according to claim 5, wherein the aliphatic acid is one of oleic acid, linoleic acid, stearic acid, myristic acid, and palmitic acid.

7. A method of preparing an amine derivative compound which is soluble in both oils and water, the method comprising:

providing one of phenylpropanolamine, fenfluramine, and 17-(cyclopropylmethyl)-4-5-epoxy-3,14-dihydroxymorphinan-6-one in free base form;

providing an oil-soluble, long-chain aliphatic acid, and reacting the amine in free base form with the aliphatic acid to form the amine derivative compound.

8. A method according to claim 7, wherein the aliphatic acid comprises one of oleic acid, linoleic acid, stearic acid, myristic acid, and palmitic acid.

* * * * *